(12) United States Patent
Müssig et al.

(10) Patent No.: US 7,616,993 B2
(45) Date of Patent: Nov. 10, 2009

(54) HEART STIMULATOR USING A BEZIER FUNCTION TO DEFINE AV-DELAY VALUES

(75) Inventors: Dirk Müssig, West Linn, OR (US); Kurt Swenson, Dayton, OR (US)

(73) Assignee: BIOTRONIK CRM Patent AG (CH)

( * ) Notice: Subject to any disclaimer, the term of this patent is extended or adjusted under 35 U.S.C. 154(b) by 395 days.

(21) Appl. No.: 11/563,296

(22) Filed: Nov. 27, 2006

(65) Prior Publication Data

US 2008/0125822 A1    May 29, 2008

(51) Int. Cl.
*A61N 1/362* (2006.01)
(52) U.S. Cl. .................................. 607/9; 607/17; 607/28
(58) Field of Classification Search ................... 607/9, 607/17, 28
See application file for complete search history.

(56) References Cited

U.S. PATENT DOCUMENTS

| | | | | |
|---|---|---|---|---|
| 5,309,919 | A | * | 5/1994 | Snell et al. .................. 600/510 |
| 6,784,886 | B1 | * | 8/2004 | Cailloux ..................... 345/440 |
| 2004/0158293 | A1 | * | 8/2004 | Yonce et al. ................... 607/9 |
| 2005/0010256 | A1 | * | 1/2005 | Scharf .......................... 607/9 |
| 2005/0137632 | A1 | | 6/2005 | Ding et al. |

FOREIGN PATENT DOCUMENTS

| | | |
|---|---|---|
| EP | 0 773 038 B1 | 5/1997 |
| WO | WO 99/13432 A | 3/1999 |
| WO | WO 03/052397 A | 6/2003 |

OTHER PUBLICATIONS

European Search Report, issued by the European Patent Office on Jan. 22, 2008 for patent application serial No. EP 07021371.5.

* cited by examiner

*Primary Examiner*—Carl H Layno
*Assistant Examiner*—Pamela M Bays
(74) *Attorney, Agent, or Firm*—Craig A. Fieschko, Esq.; DeWitt Ross & Stevens S.C.

(57) ABSTRACT

A heart stimulator provides for a more appropriate yet simple setting of the AV-delay. The heart stimulator comprises a stimulation pulse generator adapted to generate electric stimulation pulses and connected to a ventricular stimulation electrode for delivering electric stimulation pulses. A sensing stage connected to an electrode for picking up electric potentials inside a ventricle is adapted to sense an excitation or a contraction of a heart chamber. A memory is adapted to store parameters defining a Bezier function determining the relationship between AV-delay values and heart rate and a control unit connected to said memory, said sensing stage and to said stimulation pulse generator, is adapted to determine an actual AV-delay based on an actual intrinsic heart rate or an actual stimulation rate and a non-linear smoothing interpolation between said parameters stored in said memory.

19 Claims, 4 Drawing Sheets

HEART STIMULATOR USING A BEZIER FUNCTION TO DEFINE AV-DELAY VALUES

FIELD OF INVENTION

The invention refers to a heart stimulator for stimulating at least one chamber of a heart by means of electrical stimulation pulses that are delivered when a delay time started by a cardiac event expires. The invention particularly refers to implantable pacemakers and implantable cardioverter/defibrillators for atrium synchronous stimulation of a ventricle of a heart.

BACKGROUND OF THE INVENTION

Implantable heart stimulators can be used for treating a variety of heart disorders like bradycardia, tachycardia or fibrillation by way of electric stimulation pulses delivered to the heart tissue, the myocardium. Strong enough a stimulation pulse outside a heart chamber's refractory period leads excitation of the myocardium of that heart chamber, which in turn is followed by a contraction of the respective heart chamber.

Depending on the disorder to be treated, such heart stimulator generates electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing and that carries a stimulation electrode in the region of its distal end. A stimulation pulse also is called a pace. Similarly, pacing a heart chamber means stimulating a heart chamber by delivery of a stimulation pulse.

In order to be able to sense a contraction a heart chamber that naturally occurs without artificial stimulation and that is called intrinsic, the heart stimulator usually comprises at least one sensing stage that is connected to a sensing electrode on said electrode placed in the heart chamber. An intrinsic excitation of a heart chamber results in characteristic electrical potentials that can be picked up via the sensing electrode and that can be evaluated by the sensing stage in order to determine whether an intrinsic excitation—called: intrinsic event—has occurred.

Usually, a heart stimulator features separate stimulation generators for each heart chamber to be stimulated. Therefore, in a dual chamber pacemaker, usually an atrial and a ventricular stimulation pulse generator for generating atrial and ventricular stimulation pulses are provided. Delivery of an atrial or a ventricular stimulation pulse causing an artificial excitation of the atrium or the ventricle, respectively, is called an atrial stimulation event $A_P$ (atrial paced event) or a ventricular stimulation event $V_P$ (ventricular paced event), respectively.

Similarly, common heart stimulators feature separate sensing stages for each heart chamber to be of interest. In a dual chamber pacemaker usually two separate sensing stages, an atrial sensing stage and a ventricular sensing stage, are provided that are capable to detect intrinsic atrial events $A_S$ (atrial sensed event) or intrinsic ventricular events $V_S$ (ventricular sensed event), respectively.

As known in the art, separate sensing and pacing stages are provided for three-chamber (right atrium RA, right ventricle RV, left ventricle LV) or four-chamber (right atrium RA, left atrium LA, right ventricle RV, left ventricle LV) pacemakers or ICDs.

By means of a sensing stage for a heart chamber to be stimulated, the pacemaker is able to only trigger stimulation pulses when needed that is when no intrinsic excitation of the heart chamber occurs in time. Such mode of pacing a heart chamber is called demand mode. In the demand mode the pacemaker schedules an atrial or a ventricular escape interval that causes triggering of an atrial or ventricular stimulation pulse when the escape interval times out. Otherwise, if an intrinsic atrial or ventricular event is detected prior to time out of the respective atrial or ventricular escape interval, triggering of the atrial or ventricular stimulation pulse is inhibited. Such intrinsic (natural, non-stimulated) excitation are manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as simultaneous events and the terms "depolarization" and "contraction" are used herein as synonyms.

In heart cycle, an excitation of the myocardium leads to depolarization of the myocardium that causes a contraction of the heart chamber. If the myocardium is fully depolarized it is unsusceptible for further excitation and thus refractory. Thereafter, the myocardium repolarizes and thus relaxes and the heart chamber is expanding again. In a typical electrogram (EGM) depolarization of the ventricle corresponds to a signal known as "R-wave". The repolarization of the ventricular myocardium coincides with a signal known as "T-wave". Atrial depolarization is manifested by a signal known as "P-wave".

A natural contraction of a heart chamber thus can be detected by evaluating electrical signals sensed by the sensing channels. In the sensed electrical signal the depolarization of an atrium muscle tissue is manifested by occurrence of a P-wave. Similarly, the depolarization of ventricular muscle tissue is manifested by the occurrence of a R-wave. A P-wave or a R-wave thus leads to an atrial sense event As or a ventricular sense event Vs, respectively.

Several modes of operation are available in a state of the art multi mode pacemaker. The pacing modes of a pacemaker, both single and dual or more chamber pacemakers, are classified by type according to a three letter code. In such code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse to a prescribed chamber of the heart a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To such three letter code, a fourth letter "R" may be added to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

A dual chamber pacemaker featuring an atrial and a ventricular sensing stage and an atrial and a ventricular stimulation pulse generator can be operated in a number of stimulation modes like VVI, wherein atrial sense events are ignored and no atrial stimulation pulses are generated, but only ventricular stimulation pulses are delivered in a demand mode, AAI, wherein ventricular sense events are ignored and no ventricular stimulation pulses are generated, but only atrial stimulation pulses are delivered in a demand mode, or DDD, wherein both, atrial and ventricular stimulation pulses are delivered in a demand mode. In such DDD mode of pacing, ventricular stimulation pulses can be generated in synchrony with sensed intrinsic atrial events and thus in synchrony with an intrinsic atrial rate, wherein a ventricular stimulation pulse is scheduled to follow an intrinsic atrial contraction after an appropriate atrioventricular delay (AV-delay; AVD), thereby maintaining the hemodynamic benefit of atrioventricular synchrony.

Since an optimal AV-delay may vary for different heart rates or stimulation rates and may even vary from patient to patient, AV-delay usually is adjustable. In order to provide individual AV-delays for different heart rates, a discrete number of e.g. 5 different AV-delay values may be programmed into the heart stimulator, each of the 5 AV-delays being provided for different range of heart rates or stimulation rates.

Alternatively, a linear relationship between a longest AV-delay for the lowest heart or stimulation rate and a shortest AV-delay for the highest allowable stimulation or heart rate may be established. The intermediate values of the AV-delay for intermediate heart rates can be linearly interpolated.

Both prior art approaches only poorly reflect the optimum dynamic behavior of a healthy heart.

SUMMARY OF THE INVENTION

It is an object of the invention to provide a heart stimulator that provides for a more appropriate yet simple setting of the AV-delay.

According to the present invention the object of the invention is achieved by a heart stimulator featuring:

a stimulation pulse generator adapted to generate electric stimulation pulses and being connected or being connectable to at least a ventricular stimulation electrode for delivering electric stimulation pulses to at least said ventricle of the heart, a sensing stage connected or being connectable to an electrode for picking up electric potentials inside at least said ventricle of a heart, said sensing stage being adapted to sense an excitation or a contraction of a heart chamber, a memory for an AV-delay setting and a control unit that is connected to said memory, said sensing stage and to said stimulation pulse generator.

The memory is adapted to store parameters defining a Bezier function determining the relationship between AV-delay values and heart rate values The control unit is adapted to determine an actual AV-delay based on an actual intrinsic heart rate or an actual stimulation rate.

Preferably, the control unit is adapted to calculate intermediate AV-delay values based on a Bezier-function according to parameters stored in said memory depending on an actual heart rate or stimulation rate.

Alternatively, the parameters stored in said memory may represent a look-up table calculated from a Bezier function, said look-up table comprising a plurality of AV-delay values each associated to a heart or stimulation rate. In such embodiment, the control unit is adapted to calculate intermediate AV-delay for those heart or stimulation rates that are not directly comprised in said memory based an linear interpolation. Instead of using a Bezier function as a non-linear smoothing interpolation between preset data points, any other suitable smoothing function could be used. However, using a Bezier function is preferred due to its ease of implementation.

A further aspect of the invention is directed to a programming device for a heart stimulator according to the invention that comprises a graphical user interface and input means connected to said graphical user interface in order to graphically define a functional relationship between the heart or stimulation rate and the AV-delay. In a preferred embodiment, a number of 3 to 16 handles are provided to set AV delay values for dedicated heart rates. The programmer further comprises a Bezier calculation unit for calculating a Bezier function based an the settings defined by the position of the handles. The handles preferably are graphical representations that can be moved by the input means. The input means may comprise a computer mouse. Alternatively, the graphical user interface is designed as a touch screen panel and thus directly serves as input means.

The programming device comprises a Bezier calculation unit in order to calculate control points of the Bezier function based on the position of the handles. Except for the first and the last control point, control points of a Bezier function are not necessary points on the curve defined by the Bezier function. The handles of the graphical user interface, however, are points on the curve defining the relationship between heart or stimulation rate and AV-delay. Therefore, the control points defining the Bezier function need to be calculated from the position of the handles.

The control points of the Bezier function are defined by two coordinates in a plane. Thus each control point is a two dimensional vector. The control points define the Bezier function in a manner known as such. According to a first embodiment of the invention, the control points are directly stored in said memory of the heart stimulator.

Alternatively, after calculating the control points of the Bezier curve and thus the Bezier curve, a selected number of AV-delay values from said Bezier curve corresponding to dedicated heart or stimulation rates are transformed into a look up table that is stored into the heart stimulator's memory. Transmission of the control points defining the Bezier curve or of the look up table from the programmer to the heart stimulator is achieved by means of transceivers for bidirectional wireless telemetric data transmission between the programmer and the heart stimulator.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
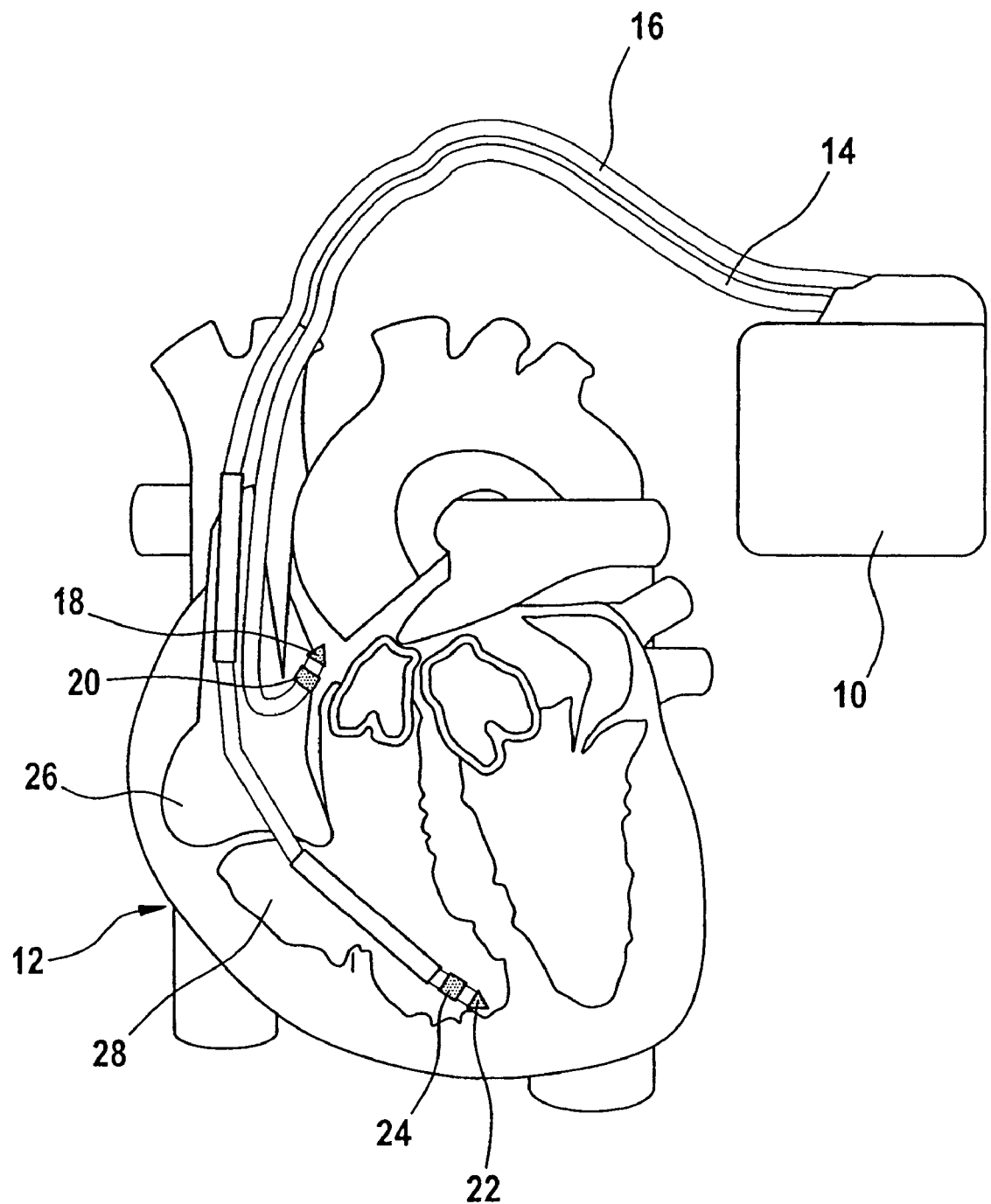
FIG. 1 shows a dual chamber pacemaker connected to leads placed in a heart.

In FIG. 1 a dual chamber pacemaker 10 as heart stimulator connected to pacing/sensing leads placed in a heart 12 is illustrated. The pacemaker 10 is electrically coupled to heart 12 by way of leads 14 and 16. Lead 14 has a pair of right atrial electrodes 18 and 20 that are in contact with the right atria 26 of the heart 12. Lead 16 has a pair of electrodes 22 and 24 that are in contact with the right ventricle 28 of heart 12. Electrodes 18 and 22 are tip-electrodes at the very distal end of leads 14 and 16, respectively. Electrode 18 is a right atrial tip electrode RA-Tip and electrode 22 is a right ventricular tip electrode 22. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring.

Figure 2:
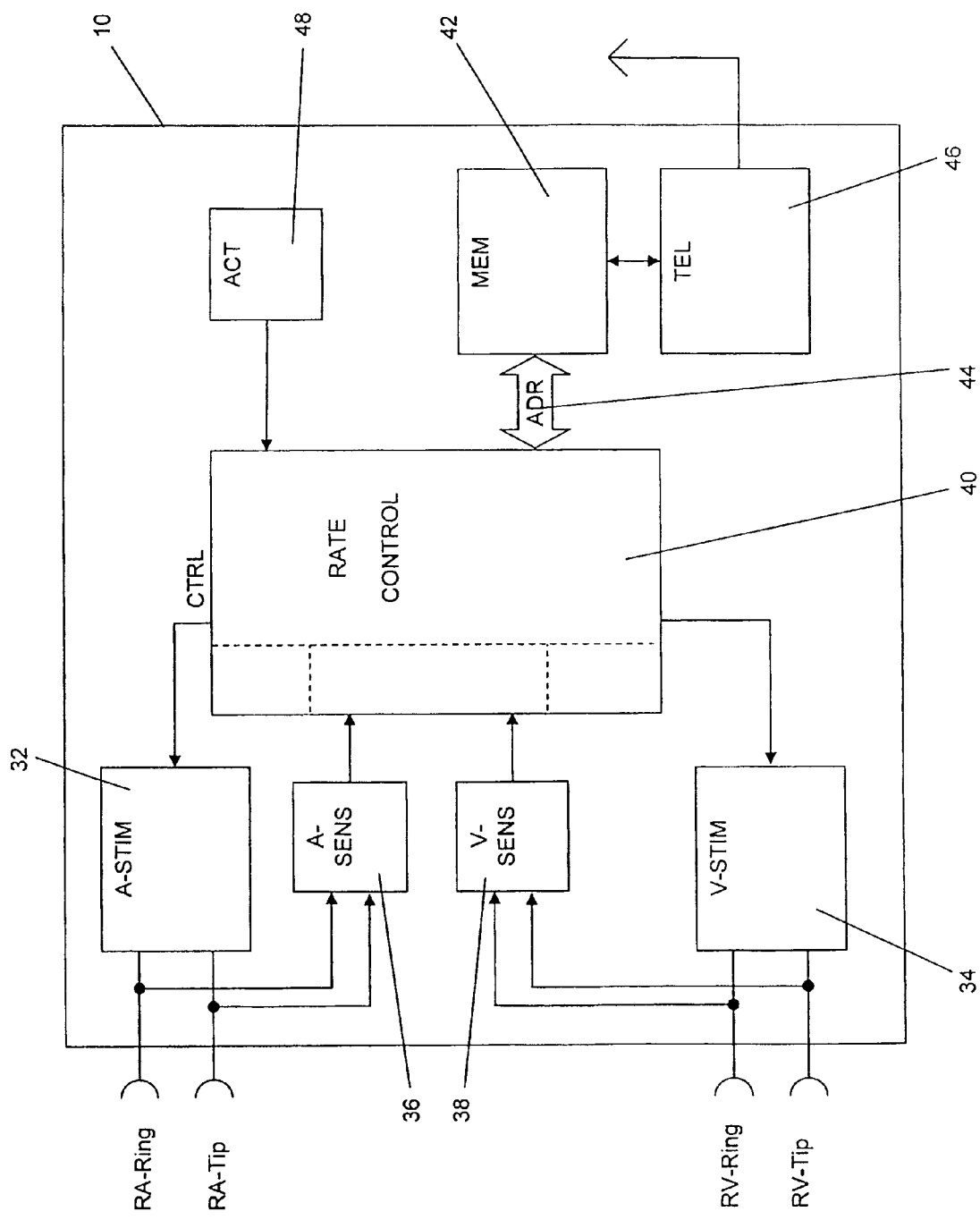
FIG. 2 is a block diagram of a heart stimulator according to the invention.

Referring to FIG. 2 a simplified block diagram of a dual chamber pacemaker 10 is illustrated. During operation of the pacemaker leads 14 and 16 are connected to respective output/input terminals of pacemaker 10 as indicated in FIG. 1 and carry stimulating pulses to the tip electrodes 18 and 22 from an atrial stimulation pulse generator A-STIM 32 and a ventricular pulse generator V-STIM 34, respectively. Further, electrical signals from the atrium are carried from the electrode pair 18 and 20, through the lead 14, to the input terminal of an atrial channel sensing stage A-SENS 36; and electrical signals from the ventricles are carried from the electrode pair 22 and 24, through the lead 16, to the input terminal of a ventricular sensing stage V-SENS 38.

Controlling the dual chamber pacer 10 is a control unit CTRL 40 that is connected to sensing stages A-SENS 36 and V-SENS 38 and to stimulation pulse generators A-STIM 32 and V-STIM 34. Control unit CTRL 40 receives the output signals from the atrial sensing stage A-SENS 32 and from the ventricular sensing stage V-SENS 34. The output signals of sensing stages A-SENS 32 and V-SENS 34 are generated each time that a P-wave representing an intrinsic atrial event or an R-wave representing an intrinsic ventricular event, respectively, is sensed within the heart 12. An As-signal is generated, when the atrial sensing stage A-SENS 32 detects a P-wave and a Vs-signal is generated, when the ventricular sensing stage V-SENS 34 detects an R-wave.

Control unit CTRL 40 also generates trigger signals that are sent to the atrial stimulation pulse generator A-STIM 36 and the ventricular stimulation pulse generator V-STIM 38, respectively. These trigger signals are generated each time that a stimulation pulse is to be generated by the respective pulse generator A-STIM 36 or V-STIM 38. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, A-SENS 32 and/or V-SENS 34, is typically disabled by way of a blanking signal presented to these amplifiers from the control unit CTRL 40, respectively. This blanking action prevents the sensing stages A-SENS 32 and V-SENS 34 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event $A_{rs}$ but ignored.

Control unit CTRL 40 comprises circuitry for timing ventricular and/or atrial stimulation pulses according to an adequate stimulation rate that can be adapted to a patient's hemodynamic need as pointed out below.

Still referring to FIG. 2, the pacer 10 may also include a memory circuit MEM 42 that is coupled to the control unit CTRL 40 over a suitable data/address bus ADR 44. This memory circuit MEM 42 allows certain control parameters, used by the control unit CTRL 40 in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM 42 for later retrieval and analysis.

Memory MEM 42 is adapted to store parameters determining the functional relationship between a heart rate or a stimulation rate as determined by control unit CTRL 40. According to a preferred embodiment, these parameters defining determining the functional relationship between a heart rate or a stimulation rate are control points of a Bezier function defining a Bezier curve that in turn defines the functional relationship between a heart rate or a stimulation rate. Control unit CTRL 40 comprises a Bezier calculation unit that is adapted to determine an AV-delay for an actual heart rate or stimulation rate based on the Bezier function that is defined by the control points stored in memory MEM 42.

A telemetry circuit TEL 46 is further included in the pacemaker 10. This telemetry circuit TEL 46 is connected to the control unit CTRL 40 by way of a suitable command/data bus. Telemetry circuit TEL 46 allows for wireless data exchange between the pacemaker 10 and some remote programming or analyzing device which can be part of a centralized service center serving multiple pacemakers.

Figure 3:
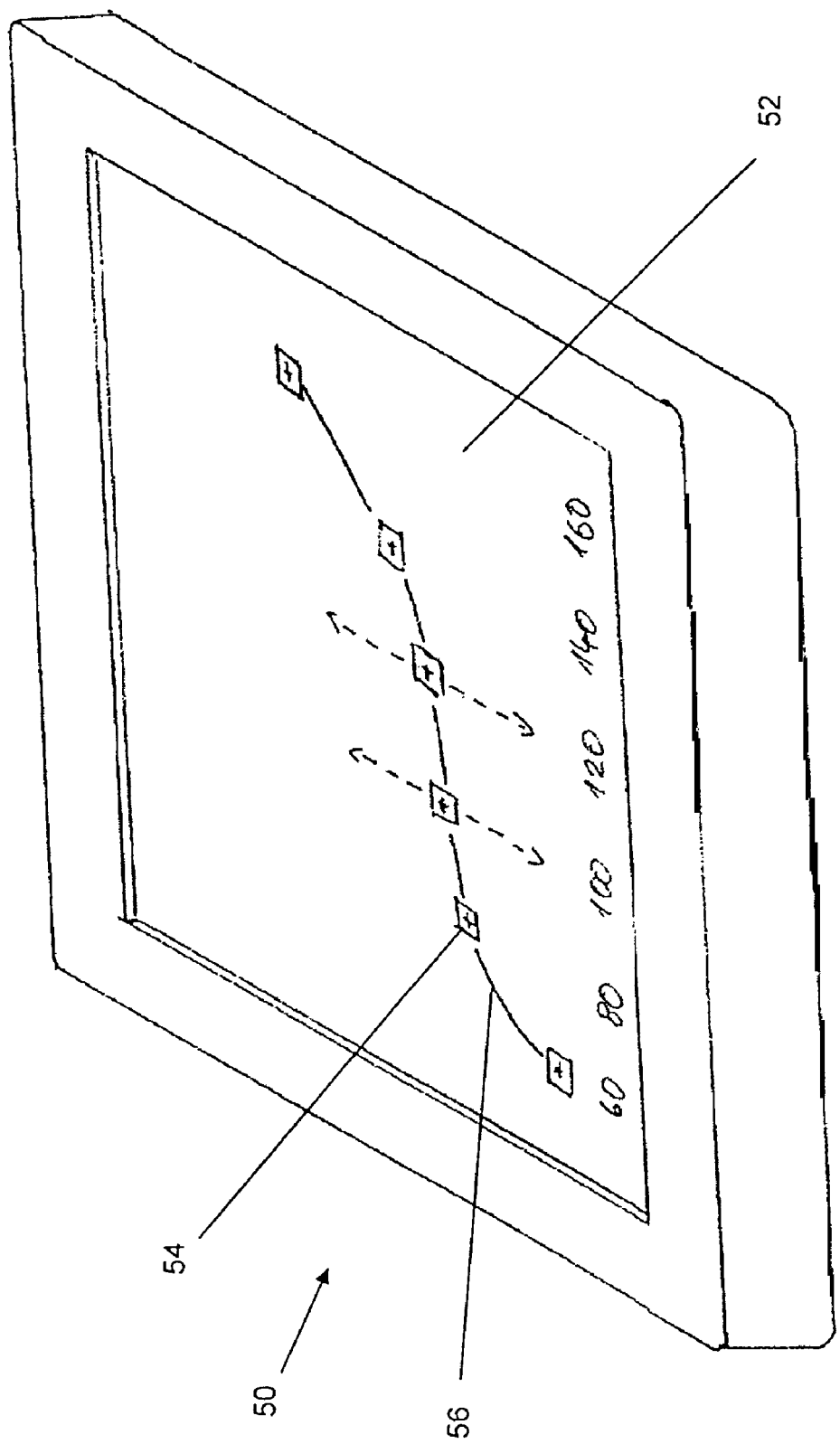
FIG. 3 is a schematic representation of programming device according to the invention.
Figure 4:
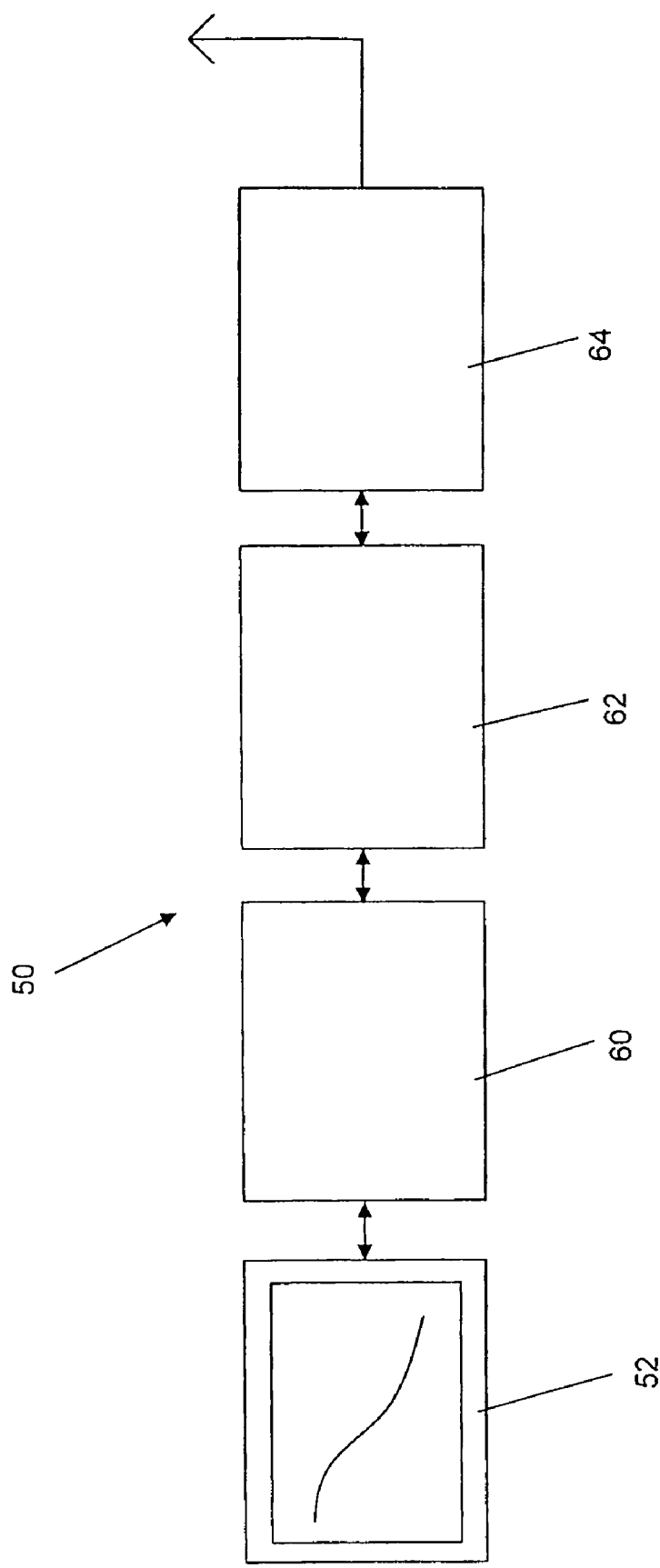
FIG. 4 is a block diagram of the programming device in FIG. 3.

In particular, by means of telemetry circuit TEL 46, control points for the Bezier function defining the functional relationship between a heart rate or a stimulation rate can be remotely received from a programming device as illustrated in FIGS. 3 and 4.

The pacemaker 10 in FIG. 1 is referred to as a dual chamber pacemaker because it interfaces with both the right atrium 26 and the right ventricle 28 of the heart 12. Those portions of the pacemaker 10 that interface with the right atrium, e.g., the lead 14, the P-wave sensing stage A-SENSE 32, the atrial stimulation pulse generator A-STIM 36 and corresponding portions of the control unit CTRL 40, are commonly referred to as the atrial channel. Similarly, those portions of the pacemaker 10 that interface with the right ventricle 28, e.g., the lead 16, the R-wave sensing stage V-SENSE 34, the ventricular stimulation pulse generator V-STIM 38, and corresponding portions of the control unit CTRL 40, are commonly referred to as the ventricular channel.

In order to allow rate adaptive pacing in a DDDR or a DDIR mode, the pacemaker 10 further includes a physiological sensor ACT 48 that is connected to the control unit CTRL 40 of the pacemaker 10. While this sensor ACT 48 is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

The control unit CTRL 40 is adapted to determine an adequate heart rate or stimulation rate in any manner known as such. The rate thus determined is used for determining an adequate AV-delay by the Bezier calculation unit based on the control points stored in memory MEM 42.

In FIG. 3, a programming device 50 for remotely programming pacemaker 10. Programming device 50 features a touch sensitive graphical display (touch screen) 52 that serves as graphical user interface and as input means. Of course, programming device 50 may comprise more further input means like buttons or scroll wheels.

Programming device 50 is displayed in its operating mode for defining the functional relationship between a heart rate or a stimulation rate by means of a Bezier curve.

Six handles 54 are provided to set an AV-delay for a dedicated heart rate. Each handle is a virtual representation on the graphical display 52 and can be each moved along an axis that is indicated by means of a dashed line. Moving of the handles 54 is effected by touching the graphical display in the are of a handle 54 to moved and moving the handle 54 to the desired position representing the AV delay for the heart rate the handle is associated to. By moving handles 54, a curve 56 is defined that represents the relationship between the heart rates or the stimulation rates and the AV-delay.

In the embodiment shown in FIG. 3, AV delays are represented in fractions of a heart cycle that is the reciprocal values of the heart rate. Therefore, curve 56 is ascending although the absolute value of the AV delay is descending when the heart rate ascends.

In an alternative embodiment, duration of the AV-delay may directly be displayed resulting in a descending curve on the graphical display 52.

It is to be noted, that the position of handles 54 define points of curve 56 itself and thus are not necessarily control points of a Bezier curve corresponding to curve 56. Therefore, the control points for Bezier curve 56 need to be calculated by means of a Bezier calculation unit 60, that is connected to the graphical display 52 and to a memory 62 and a telemetry unit 64 of the programming device 50; see FIG. 4.

Once calculated, the control points of the Bezier curve representing the functional relationship between the heart rate and the AV-delay, the control points are stored in memory 62 and can be transmitted to pacemaker 10 whenever a remote data transmission is established between programming device 50 and pacemaker 10.

What is claimed is:

1. A heart stimulator for stimulating at least a ventricle of a heart, the heart stimulator comprises:
    a stimulation pulse generator adapted to generate electric stimulation pulses and being connected or being connectable to at least a ventricular stimulation electrode for delivering electric stimulation pulses to at least said ventricle of the heart,
    a sensing stage connected or being connectable to an electrode for picking up electric potentials inside at least said ventricle of a heart, said sensing stage being adapted to sense an excitation or a contraction of a heart chamber,
    a control unit that is connected to a memory, to said sensing stage and to said stimulation pulse generator,
    wherein said memory is adapted to store parameters defining a Bezier function determining the relationship between AV-delay values and heart rate and the control unit is adapted to determine an actual AV-delay based on an actual intrinsic heart rate or an actual stimulation rate and a non-linear smoothing interpolation between said parameters stored in said memory.

2. The heart stimulator according to claim 1, wherein said parameters stored in said memory define a Bezier function wherein said control unit is adapted to calculate an actual AV-delay based on the Bezier function defined by said parameters stored in said memory and an actual heart or stimulation rate.

3. The heart stimulator according to claim 2, wherein said parameters defining a Bezier function are control points of a Bezier curve.

4. The heart stimulator according to claim 2 or 3, wherein the control unit is adapted to calculate intermediate AV-delay values based on a Bezier function according to parameters stored in said memory depending on an actual heart rate or stimulation rate.

5. The heart stimulator according to claim 1, wherein the parameters stored in said memory represent a look-up table calculated from a curve representing a non-linear smoothing interpolation between preset data points, said look-up table comprising a plurality of AV-delay values each associated to a heart or stimulation rate range.

6. The heart stimulator according to claim 5, wherein the control unit is adapted to calculate intermediate AV-delay for those heart or stimulation rates that are not directly comprised in said memory based on a linear interpolation.

7. A heart stimulator for stimulating at least a ventricle of a heart, the heart stimulator comprising:
    a stimulation pulse generator adapted to generate electric stimulation pulses and being connected or being connectable to at least a ventricular stimulation electrode for delivering electric stimulation pulses to at least said ventricle of the heart,
    a sensing stage connected or being connectable to an electrode for picking up electric potentials inside at least said ventricle of a heart, said sensing stage being adapted to sense an excitation or a contraction of a heart chamber,
    a control unit that is connected to a memory, to said sensing stage and to said stimulation pulse generator,
    wherein said memory is adapted to store parameters defining a Bezier function determining the relationship between AV-delay values and heart rate and the control unit is adapted to determine an actual AV-delay based on an actual intrinsic heart rate or an actual stimulation rate and a non-linear smoothing interpolation between said parameters stored in said memory,
    and a programming device comprising a graphical user interface and input means connected to said graphical user interface in order to graphically define a functional relationship between the heart or stimulation rate and the AV-delay and a Bezier calculation unit for calculating a Bezier function based on the graphical definition of the functional relationship between the heart or stimulation rate and the AV-delay displayed on said graphical user interface.

8. The heart stimulator according to claim 7, wherein the graphical user interface of said programming device is adapted to display a plurality of virtual handles for shaping a curve representing functional relationship between the heart or stimulation rate and the AV-delay and wherein the programming device comprises input means that are operationally connected to said handles and that are adapted to move the handles so as to adjust the AV-delay for a heart or stimulation rate that is assigned to a respective handle.

9. The heart stimulator according to claim 8, wherein the input means of said programming device is a computer mouse.

10. The heart stimulator according to claim 8, wherein the input means of said programming device is a touch screen that is part of the graphical user interface.

11. A heart stimulator for stimulating at least a ventricle of a heart, the heart stimulator including:
   a. a stimulation pulse generator generating electric stimulation pulses for delivery to a ventricular stimulation electrode at a stimulation rate;
   b. a sensing stage sensing excitation or a contraction of a heart chamber, and thereby sensing a measure of actual heart rate;
   c. a memory storing parameters defining a Bezier function determining the relationship between AV-delay values and the measure of actual heart rate,
   d. a control unit connected in communication with the memory, the sensing stage and the stimulation pulse generator, the control unit determining an actual AV-delay based on:
      (1) the Bezier function defined by the parameters stored in the memory, and
      (2) one or more of:
         (a) the measure of actual heart rate, and
         (b) the stimulation rate.

12. The heart stimulator of claim 11 wherein the control unit determines the actual AV-delay based on:
   a. the Bezier function defined by the parameters stored in the memory, and
   b. the measure of actual heart rate.

13. The heart stimulator of claim 11 wherein the control unit determines the actual AV-delay based on:
   a. the Bezier function defined by the parameters stored in the memory, and
   b. the stimulation rate.

14. The heart stimulator of claim 11 wherein the parameters defining the Bezier function are control points of a Bezier curve.

15. The heart stimulator of claim 11 wherein the parameters defining the Bezier function represent a look-up table including a number of AV-delay values, each AV-delay value being associated with a heart or stimulation rate range.

16. A heart stimulation system for stimulating at least a ventricle of a heart, the system comprising a heart stimulator including:
   a. a stimulation pulse generator generating electric stimulation pulses for delivery to a ventricular stimulation electrode at a stimulation rate;
   b. a sensing stage sensing excitation or a contraction of a heart chamber, and thereby sensing a measure of actual heart rate;
   c. a memory storing parameters defining a Bezier function determining the relationship between AV-delay values and the measure of actual heart rate,
   d. a control unit connected in communication with the memory, the sensing stage and the stimulation pulse generator, the control unit determining an actual AV-delay based on:
   (1) the Bezier function defined by the parameters stored in the memory, and
   (2) one or more of:
      (a) the measure of actual heart rate, and
      (b) the stimulation rate;
   e. a programming device including:
      (1) a graphical user interface, and
      (2) an input device connected to the graphical user interface, and
      (3) a Bezier calculation unit, wherein:
         (a) a user may use the graphical user interface to graphically define a functional relationship between:
            i. the AV-delay, and
            ii. the heart or stimulation rate, and
         (b) the Bezier calculation unit calculates the Bezier function based on the graphical definition of the functional relationship between the AV-delay and the heart or stimulation rate.

17. The heart stimulation system of claim 16 wherein:
   (1) the graphical user interface displays virtual handles for shaping a curve representing the functional relationship between:
      (a) the AV-delay, and
      (b) the heart or stimulation rate, and
   (2) the input device of the programming device uses motion input to impart corresponding motion to the virtual handles, thereby allowing alteration of the AV-delay for a heart or stimulation rate assigned to a respective handle.

18. The heart stimulation system of claim 16 wherein the input device is a computer mouse.

19. The heart stimulation system of claim 16 wherein the input device is a touch screen provided as part of the graphical user interface.

* * * * *